United States Patent [19]

Sherwin

[11] Patent Number: 6,032,534
[45] Date of Patent: Mar. 7, 2000

[54] ULTRASONIC APPARATUS AND METHOD OF SIMULTANEOUSLY INSPECTING MICROCOMPONENTS FOR DEFECTS

[75] Inventor: Alan Sherwin, Alexandria, Va.

[73] Assignee: Sonix, Inc., Va.

[21] Appl. No.: 09/119,000

[22] Filed: Jul. 20, 1998

[51] Int. Cl.[7] .................................................. G01N 29/04
[52] U.S. Cl. .......................................................... 73/628
[58] Field of Search .............................. 73/628, 625, 626, 73/597, 598, 599, 600

[56] References Cited

U.S. PATENT DOCUMENTS

| | | | |
|---|---|---|---|
| 5,079,951 | 1/1992 | Raymond et al. | 73/597 |
| 5,600,068 | 2/1997 | Kessler et al. | 73/620 |
| 5,684,252 | 11/1997 | Kessler et al. | 73/618 |

*Primary Examiner*—John E. Chapman
*Attorney, Agent, or Firm*—Evenson, McKeown, Edwards & Lenahan, P.L.L.C.

[57] ABSTRACT

An apparatus and method of locating defects within microcomponents using ultrasonic technology. A pulse-echo mode transducer and a through-transmission mode transducer are arranged around a component in order to introduce ultrasonic sound waves to perform inspections of both sides of the component to be tested which reduces the overall testing time by simultaneously providing a composite image of both sides of the component. By eliminating a scan process, an increase of the rate at which components are inspected is achieved.

24 Claims, 12 Drawing Sheets

PULSE-ECHO MODE
C-SCAN

THROUGH-TRANSMISSION MODE
C-SCAN

ULTRASONIC APPARATUS AND METHOD OF SIMULTANEOUSLY INSPECTING MICROCOMPONENTS FOR DEFECTS

BACKGROUND OF THE INVENTION

The present invention relates to an apparatus and method of locating defects, discontinuities, nonconformities and the like (collectively, locations of interest) within objects such as microcomponent devices using ultrasonic technology. More particularly, the present invention relates to an apparatus which comprises a pulse-echo (PE) mode transducer and a through-transmission (TT) mode transducer arranged around a microcomponent in order to introduce ultrasonic sound waves for inspection of the devices to find locations of interest therein.

Ultrasound has long been used for a variety of applications. An example of one such use is in the medical field to obtain two-dimensional soft tissue images. Ultrasound is also widely used in the semiconductor industry (i.e., component testing). For example, two frequently used techniques for non-destructive ultrasonic inspections are pulse-echo mode and through-transmission mode. The PE mode uses a single ultrasonic transducer to launch an ultrasonic impulse into the component to be inspected, and also to receive the reflected echoes. The TT mode uses two transducers facing each other, but on opposite sides of the component to be inspected. In the TT mode, one transducer launches the ultrasonic impulse, while the other transducer receives energy that is transmitted through the component.

Images created using these two techniques contain different types of information regarding the component under inspection, and therefore it is often useful to perform both types of inspection. Nevertheless, two separate inspections are normally required because these two techniques require different connections of the transducers to the ultrasonic instrument (Pulser/Receiver or P/R). I have recognized that this involves considerable additional expense and inspection times, both of which are undesirable when manufacturing components in large batch runs.

Furthermore, in some applications, a single PE image does not provide complete information, because internal structures in the component under inspection may "mask" structures at a greater depth. In this case, it is useful to examine the component using the PE mode from the opposite side as well, so that the two PE images permit a more complete analysis of the component. However, this approach also involves additional expense in using conventional inspection equipment.

U.S. Pat. No. 5,684,252 describes a method and apparatus for non-destructive ultrasonic inspection of integrated circuits or other electronic components laid out in a fixed pattern on a liquid-permeable tray using the above previously described method. I have also recognized that this method lacks the advantages of the present invention because it fails to reduce total manufacturing times by performing simultaneously inspections for defects. Thus, this method also entails high manufacturing costs due to the need to perform dual inspections.

SUMMARY OF THE INVENTION

I have further recognized that a considerable advantage can be gained if both the PE and the TT measurements are made simultaneously with a consequent increased throughput, lower manufacturing costs, etc.

In view of the forgoing, it is therefore an object of the present invention to perform simultaneous inspections at both sides of the component to be tested by providing an apparatus which allows the simultaneous inspection of both sides of a component under test. Consequently, my approach has the advantage of doubling the rate at which components can be tested.

This and other objects and advantages are achieved by the apparatus according to an embodiment of the present invention, in which two ultrasonic transducers are mounted on a fixture and are permitted to travel freely throughout the scan area, without collision with the component under inspection or its supporting fixture. The transducers are mechanically aligned to optimize the transmission of energy from the sending unit to the receiving unit.

The transducer used for the PE mode is attached to a standard ultrasonic pulser/receiver. The TT mode transducer is attached to an ultrasonic receiver (no pulser function is required on the TT side). The output signals from the two receivers are combined using a passive analog mixer. The mixer output is fed to a device, which (under software control) performs acquisition and signal processing required for producing the PE and TT images. The images are subsequently displayed on the controlling PC's monitor. The software can also perform image analysis functions to grade the components under test.

The two signals must be separated slightly in time so that they can be analyzed separately and not interfere with each other. To accomplish this, the two transducers use slightly different focal lengths and are positioned at slightly different distances ("water paths") from the surface of the component under test. The time required for the signal to arrive at each transducer is different, because the PE signal does not occur at the same point in time as the TT signal.

In another embodiment of the present invention, the transducers used for simultaneous PE/TT are electronically switched so that the PE transducer is located on the opposite side of the component, without physical movement of the component or the transducer. This enables the construction of an image of the tested component which is displayed on the monitor of the controlling computer.

In order to execute the PE scan from the opposite side, the transducers are connected to the ultrasonic instruments through a set of electronically controlled reversing switches. When a control signal is applied to the relays, the connections of the PE and TT transducers to their respective instruments are interchanged.

Another embodiment of the present invention combines pulse echo mode from both sides and through-transmission mode in a single scan. The switching network of the previous embodiments permits a single pulser-receiver to control the PE transducers on either side of the component under inspection. This technique requires two scans to completely inspect the component: the first scan accomplishes PE and TT from a first side, and the second scan accomplishes PE from a second side. The current contemplated embodiment permits all three inspection modes to be accomplished in a single scan. This maximizes throughput for high-speed production applications.

In the current embodiment, two pulser/receivers are used (i.e., one for each transducer). The outputs of the receivers are combined using a passive analog mixer. The mixer output is fed to a device, which (under software control) performs acquisition and signal processing required for producing the PE and TT images. The images are subsequently displayed on the controlling PC's monitor. The software can also perform image analysis functions to grade the components under test.

The trigger output from the device is connected to both pulsers. In addition, a variable delay circuit is installed between the trigger output and one of the pulsers. The delay is adjusted so that the two pulsers are not triggered simultaneously. The trigger output from the device causes the pulser to output the "Initial Pulse" which is used to energize the transducer so it can produce the ultrasonic impulse used in the inspection. The present embodiment allows time separation of the combined signals that correspond to each inspection mode which permits a subsequent independent analysis of the signals, even though they are displayed as a single waveform on the oscilloscope or other display device.

Another object of the present invention is to increase the rate at which components may be inspected by eliminating a scan process.

BRIEF DESCRIPTION OF THE DRAWINGS

Other objects, advantages and novel features of the present invention will become apparent from the following detailed description of the invention when considered in conjunction with the accompanying drawings wherein.

DETAILED DESCRIPTION OF THE DRAWINGS

Figure 1:
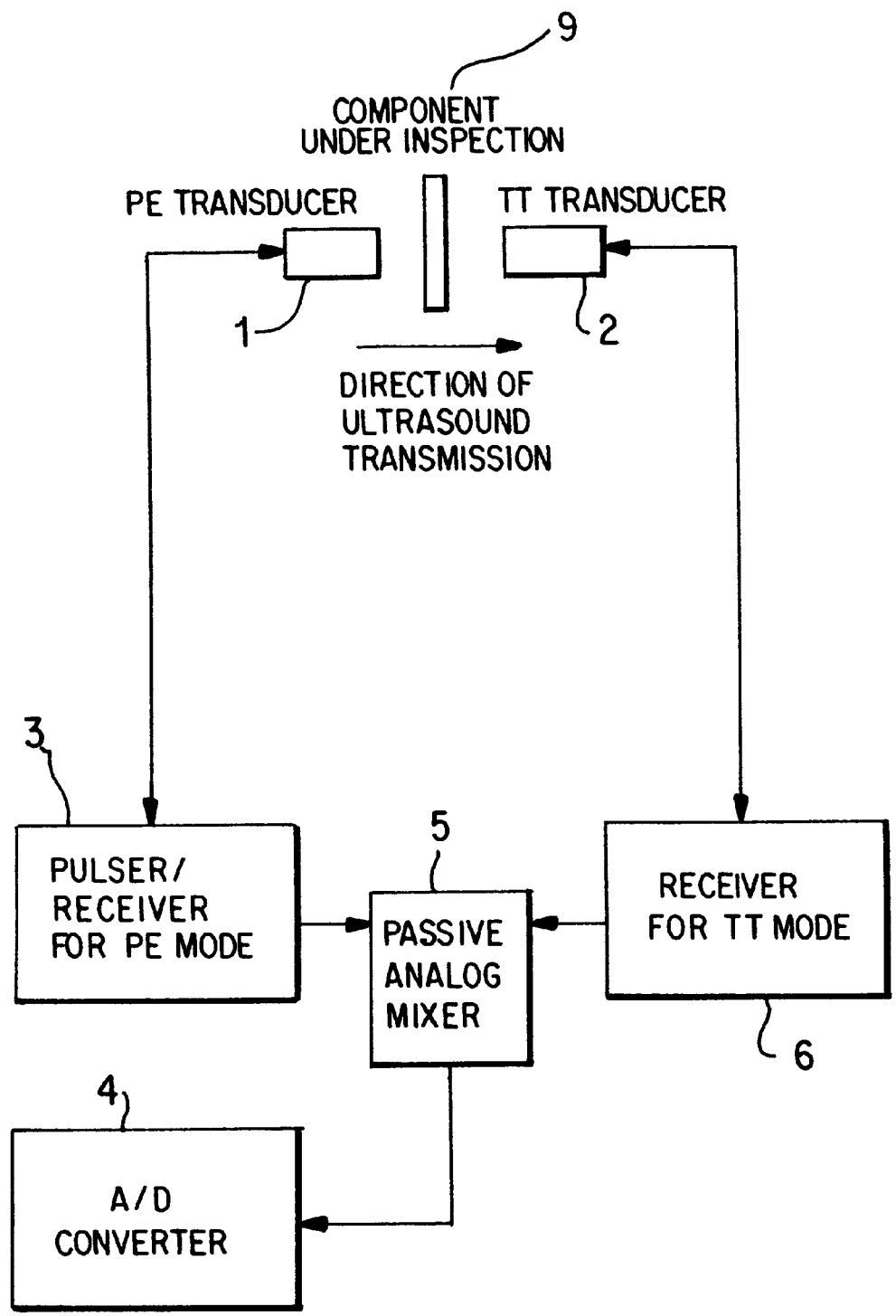
FIG. 1 is a block diagram of the basic embodiment of the simultaneous PE/TT system according to the present invention.
Figure 12A:
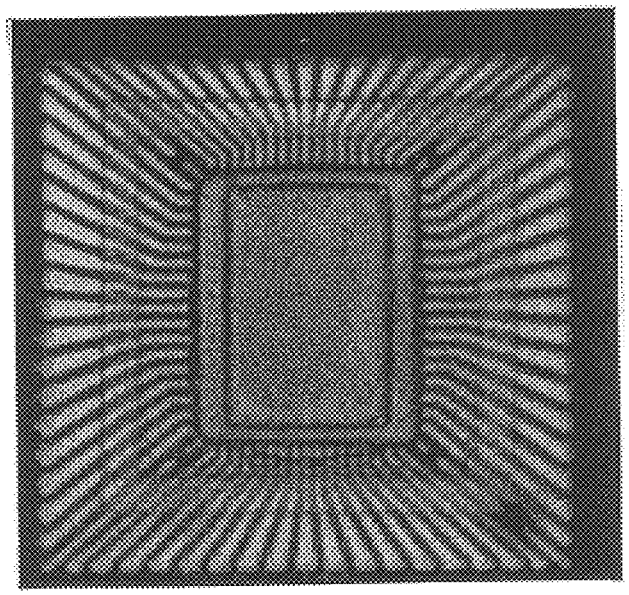
FIG. 12(a) is a computer generated display of a typical TT mode C-Scan.
Figure 12B:
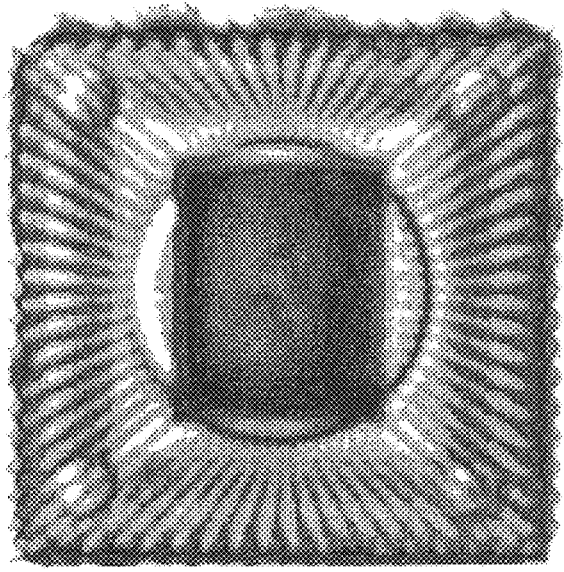
FIG. 12(b) is a computer generated display of a typical PE mode C-Scan.

In FIG. 1, a known type of PE transducer 1 used for the PE mode is attached to a standard ultrasonic pulser/receiver 3, typically a Model DPR002S pulser/receiver manufactured by JSR Electronics. The transducer 1 is arranged on one side of a component 9 (e.g., a semiconductor device) to be tested and is connected to a pulser/receiver 3. Arranged on the opposite side of the tested component 9 is a known type of TT transducer 2 which is attached to an ultrasonic receiver 6. The output signals from the two receivers 3, 4 are combined using a conventional passive analog mixer 5 (typically a standard Model No. 15542 manufactured by Mini Circuits Labs). The PE mode transducer and the TT mode transducer are, for instance, a Model V313 (manufactured by Panametrics). The mixer output is fed to a device 4, which performs the acquisition and signal processing required for producing the PE and TT images. An exemplary device used in the present invention is an A/D converter, a digitizer or an analog peak detector. These images, called C-Scans, are subsequently displayed on a controlling PC's monitor, as shown in FIGS. 12(a) and (b), for example.

Figure 2:
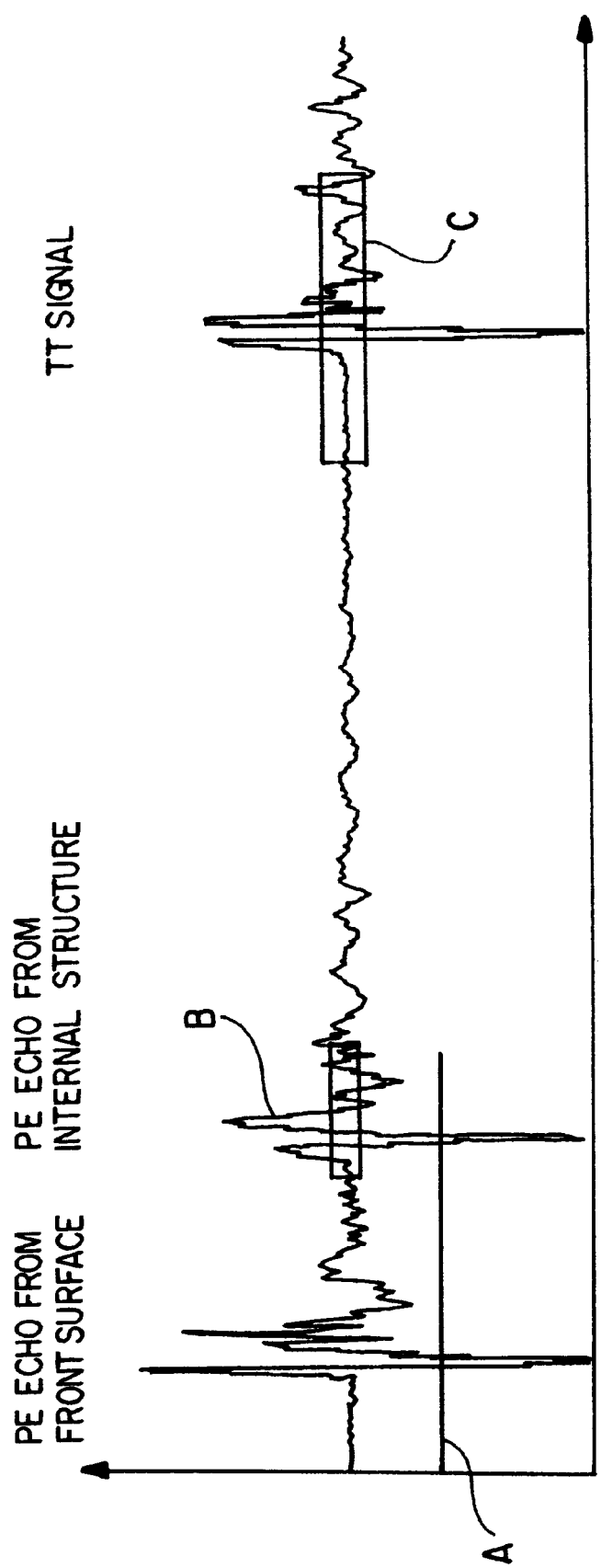
FIG. 2 is an oscilloscope display of typical combined PE and TT waveforms obtained from the system of FIG. 1.

FIG. 2 is a depiction of an oscilloscope screen display showing typical combined PE and TT waveforms obtained with an embodiment of the present invention. The TT signal is separated in time from the PE signals because the two transducers are positioned with different water path distances. As shown, reference numerals A, B and C designate computer controlled gates. Gate A is a front-surface-following gate and sets the reference point between the water and surface of the component 9 to be tested. Additionally, gate A defines the area where a front surface signal would be expected to occur. Gate B follows the front surface signal. That is, Gate B provides an indication of the signals reflected by the component 9 to be tested. Gate C does not front-surface-follow, but instead provides an indication of the TT signal, i.e., the signals that pass through the component 9 to be tested. By selecting the gate width, gate position and, where applicable, the gate threshold, the gates provide the ability to effectively isolate the signal of interest and thus select areas of the component to be tested that have meaningful information.

Figure 3:
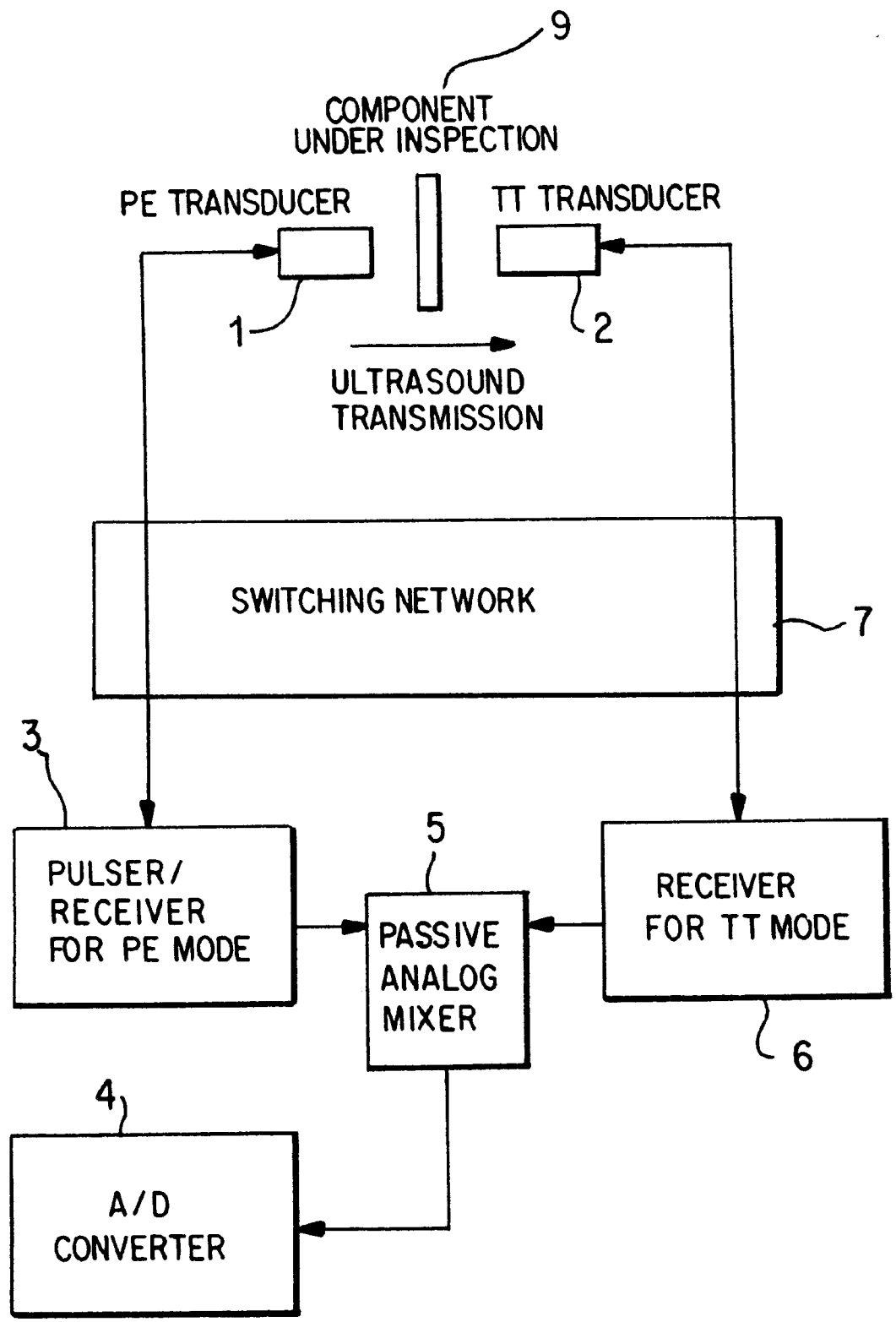
FIG. 3 is a schematic block diagram of a switching network configured for the PE/TT system of FIG. 1 from side 1 of a component under inspection according to the present invention.
Figure 4:
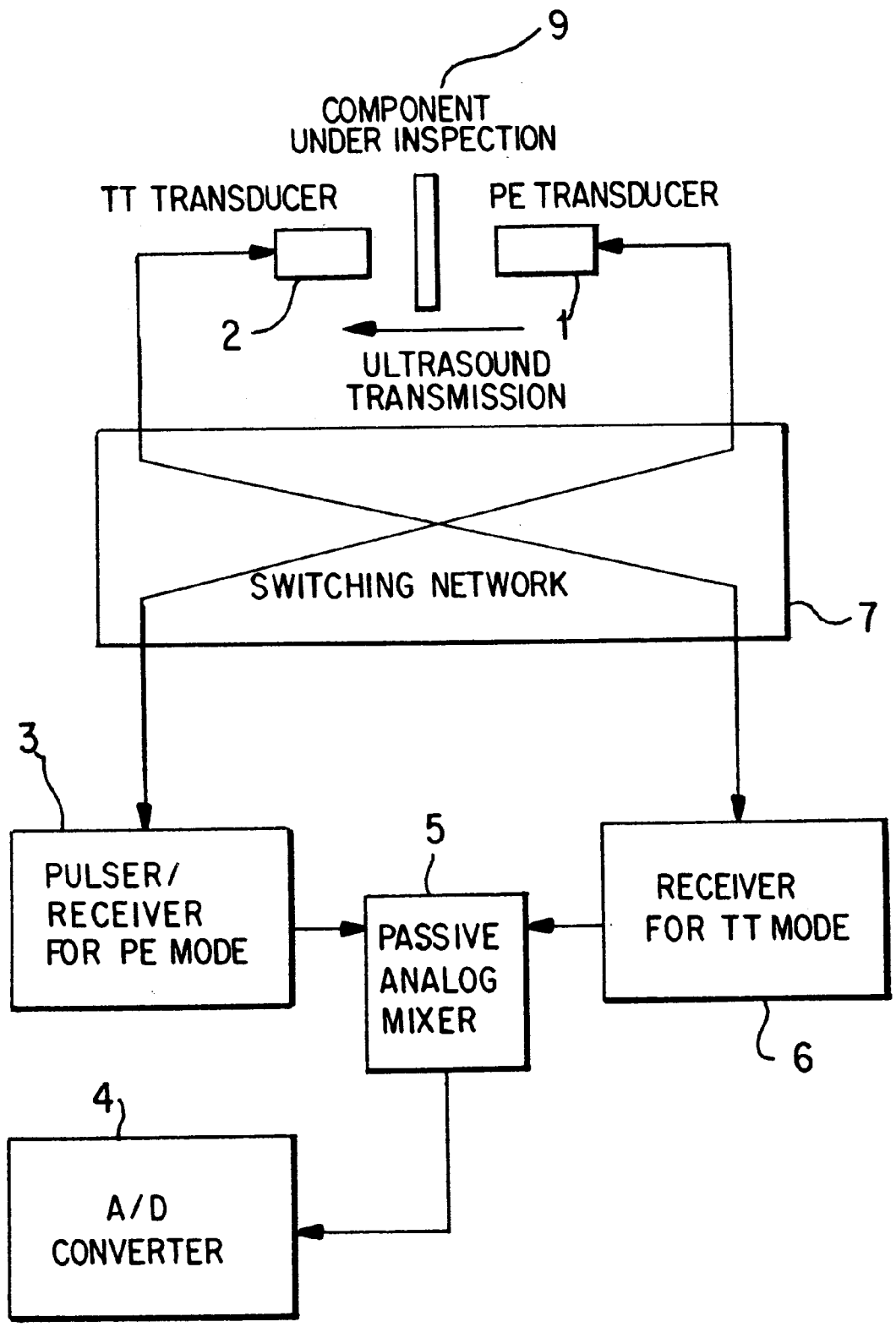
FIG. 4 is a schematic block diagram of the PE/TT transducers interchanged for PE imaging from side 2 of the component under inspection according to the present invention.

A switching network 7 connected to the pulser/receiver 3, the ultrasonic receiver 6 and both transducers 1, 2, enables selective PE/TT inspection (i.e., normal mode, reverse mode) of the inspected component 9, as shown in FIG. 3. In the reverse mode, as shown in FIG. 4, the PE/TT transducers are interchanged for PE imaging from the opposite side of the inspected component 9.

Figure 5:
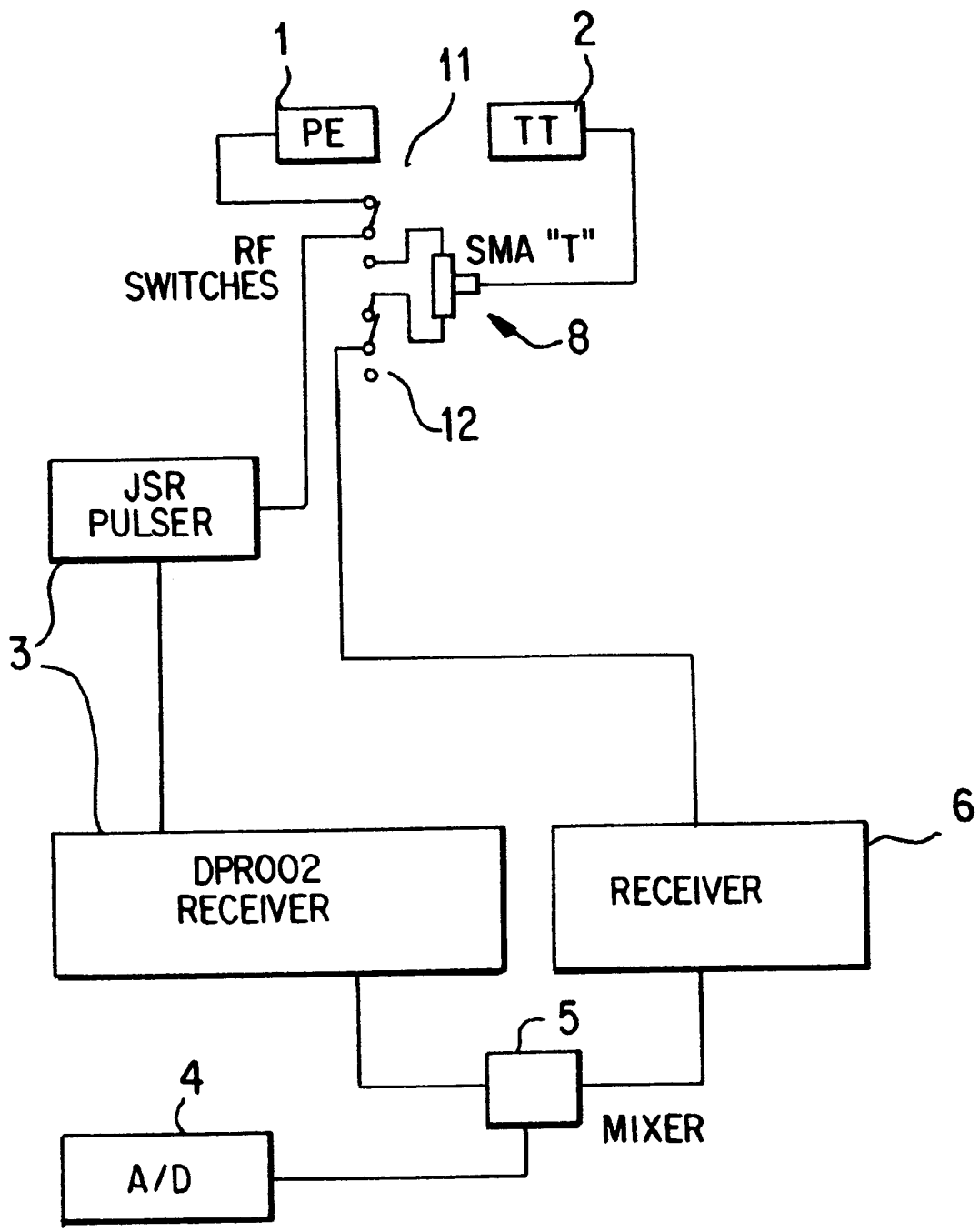
FIG. 5 is a schematic block diagram depicting the switching arrangement for normal PE mode according to the present invention.
Figure 6:
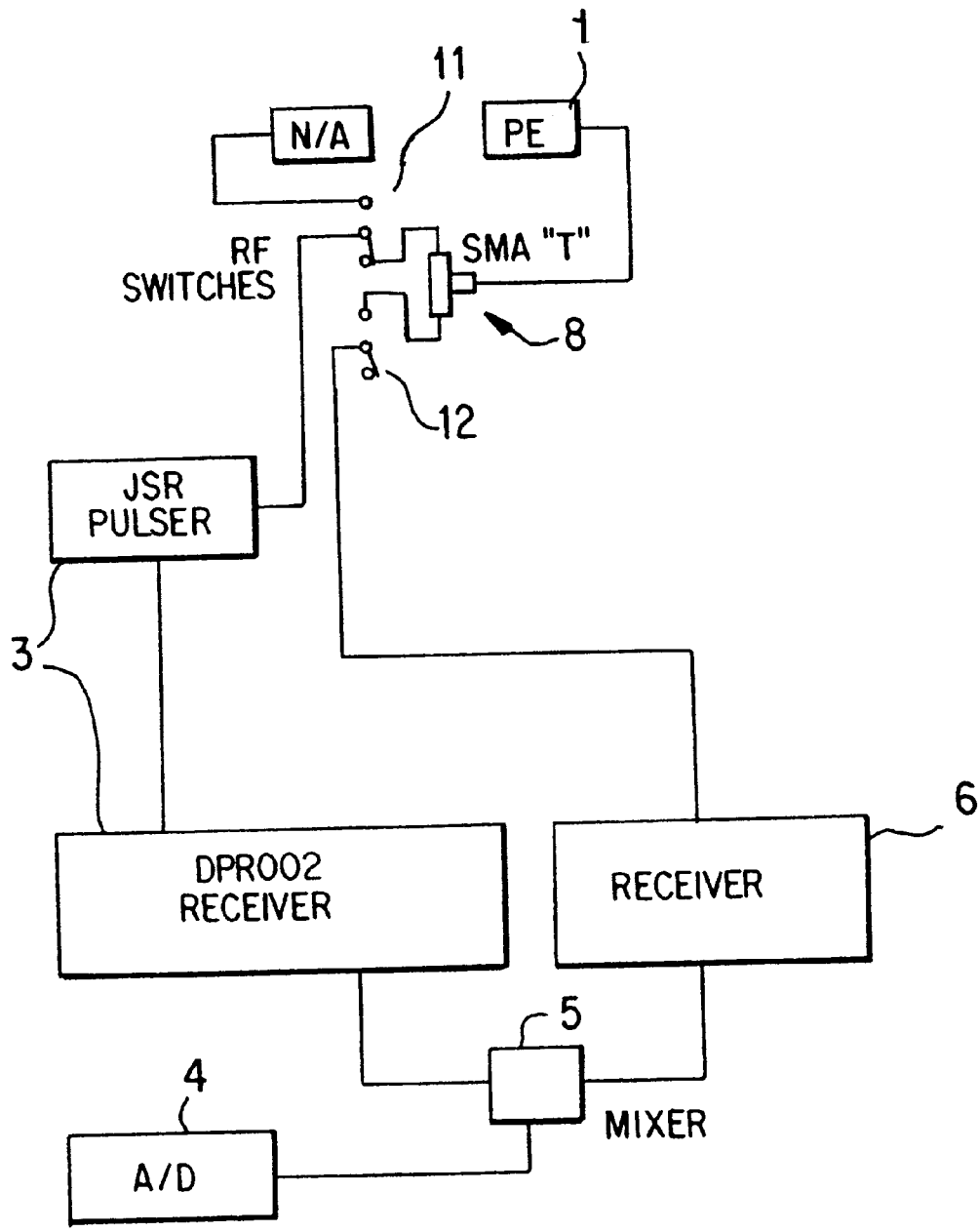
FIG. 6 is a schematic block diagram depicting the switching arrangement for the reverse PE mode according to the present invention.

FIGS. 5 and 6 show the configuration of the switching network 8 for normal PE mode and reverse PE mode, respectively. A single adapter 8 is connected to switches 11 and 12 (typically RF switches Model No. SR-2-MINHTL manufactured by RLC Electronics, for example) to implement switching between normal PE mode and reverse PE mode. In reverse mode, as shown in FIG. 6, TT imaging is not required because the TT image contains no information that was not obtained during the normal TT mode scan.

Figure 7:
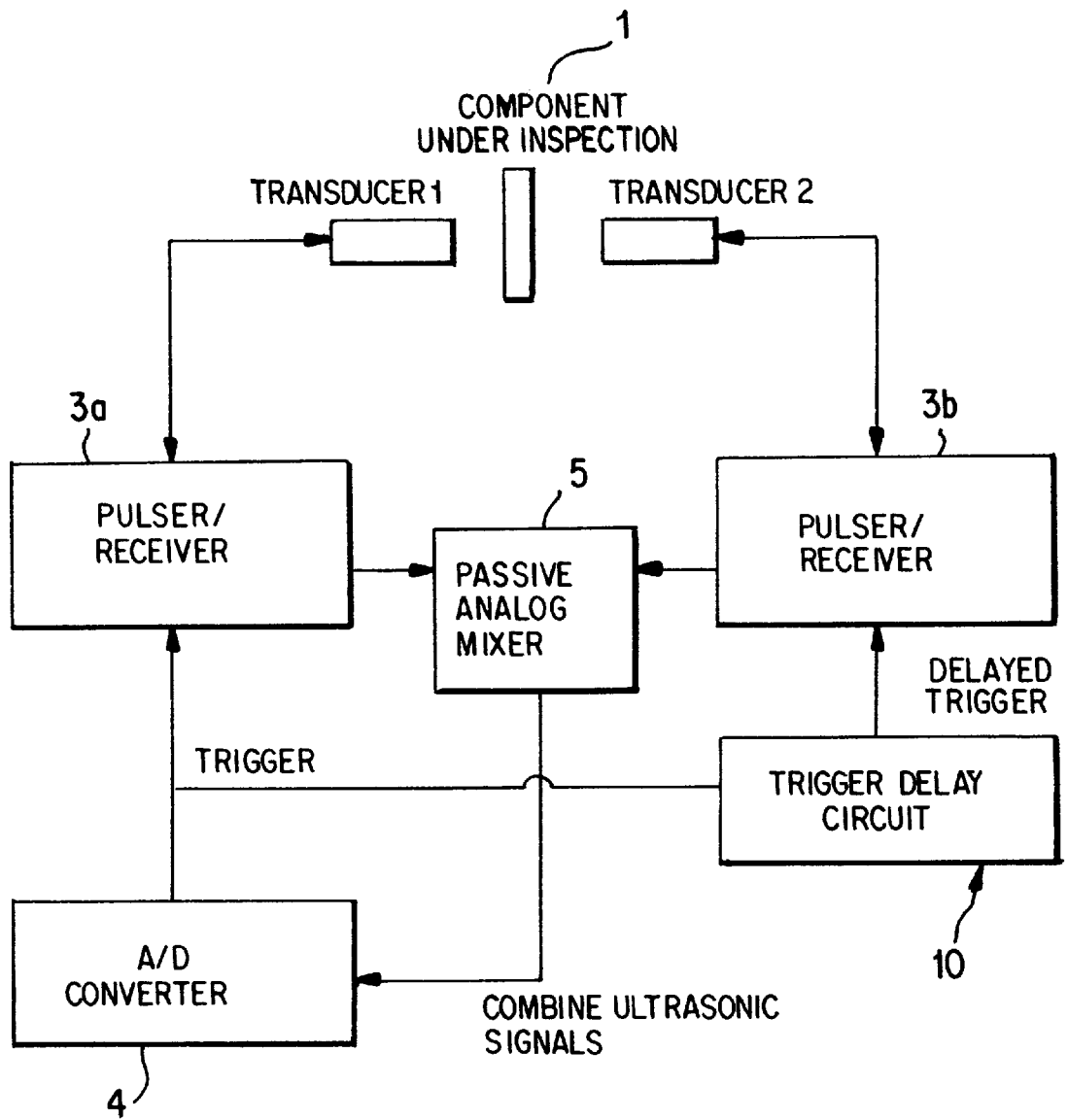
FIG. 7 is another embodiment of a schematic block diagram depicting the PE/TT system according to the invention.

In the embodiment shown in FIG. 7, a transducer 1 for each inspection mode is attached to a first standard ultrasonic pulser/receiver 3a. The transducer 1 is arranged on one side of a component 9 (e.g., a semiconductor device) to be tested and is connected to a pulser/receiver 3a. Arranged on the opposite side of the tested component 9 is a transducer 2 which is attached to a second ultrasonic pulser/receiver 3b. The output signals from the two receivers 3a, 3b are combined using a conventional passive analog mixer 5. The output of the mixer 5 is fed to device 4, which performs the acquisition and signal processing required for producing combined images. These images, called C-Scans, are subsequently displayed on a controlling PC's monitor, as shown in FIGS. 12(a) and (b), for example.

The trigger output from the device 4 is connected to the pulser/receivers 3a, 3b. A variable delay circuit 10 is connected to the trigger output of the device 4 and one of the pulsers. The delay time of the delay circuit 10 is adjusted so that the pulser/receivers 3a, 3b are not triggered simultaneously. The trigger output from the device 4 causes the pulser/receiver 3a to output an "Initial Pulse" which is used to energize the transducer 1 so that it can produce the ultrasonic impulse used during the inspection.

Figure 8:
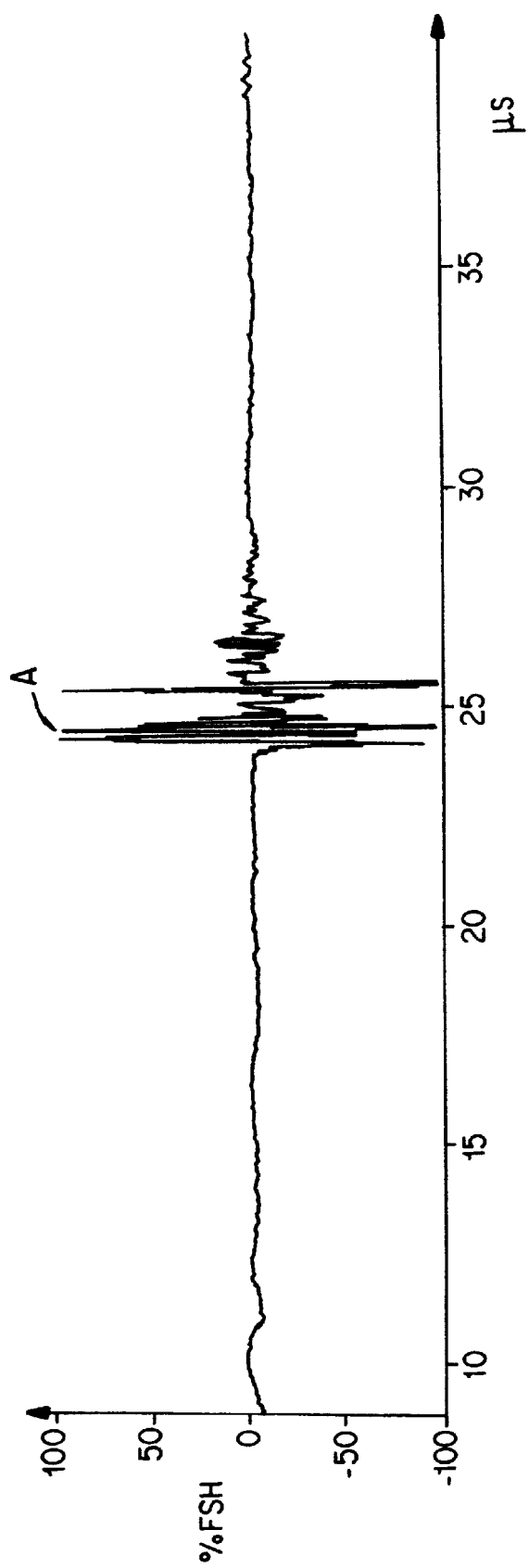
FIG. 8 is an oscillograph of a PE mode waveform from transducer 1, showing return echoes from the component under test obtained from the system of FIG. 7.
Figure 9:
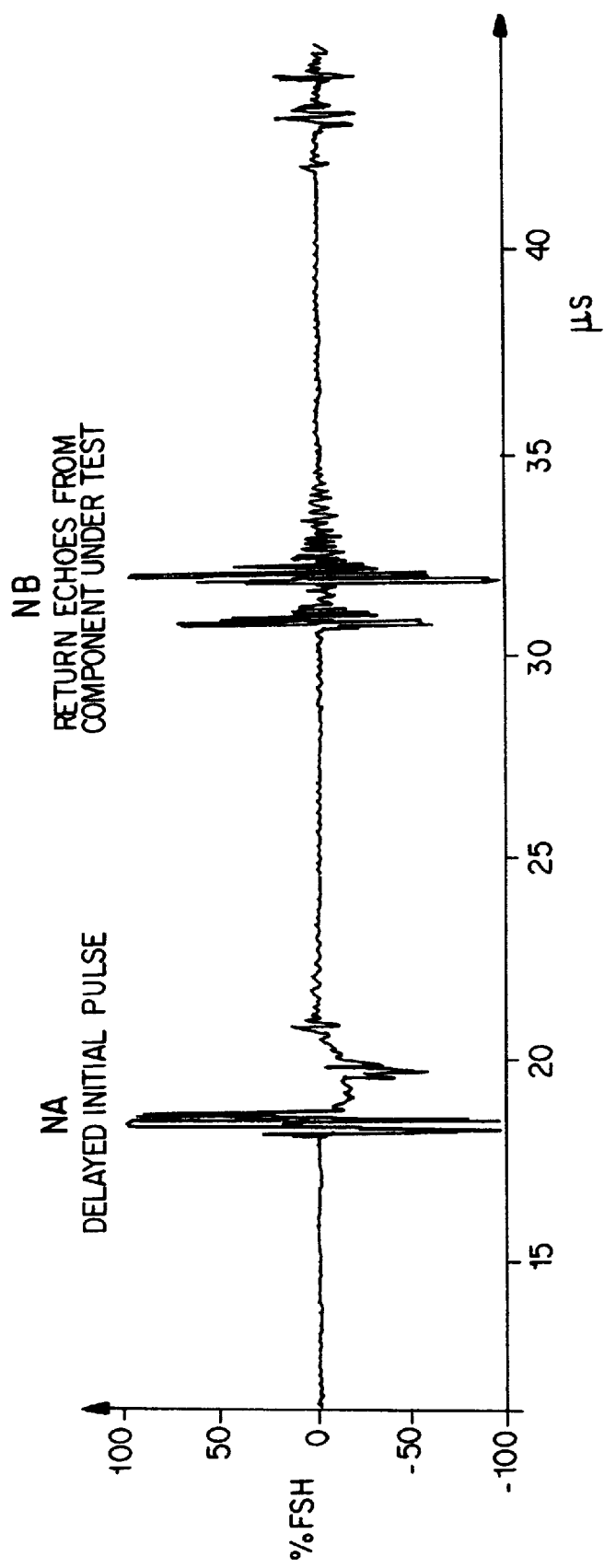
FIG. 9 is an oscillograph of a PE mode waveform from transducer 2 showing the delayed initial pulse echoes from the component under test by the system of FIG. 1.
Figure 10:
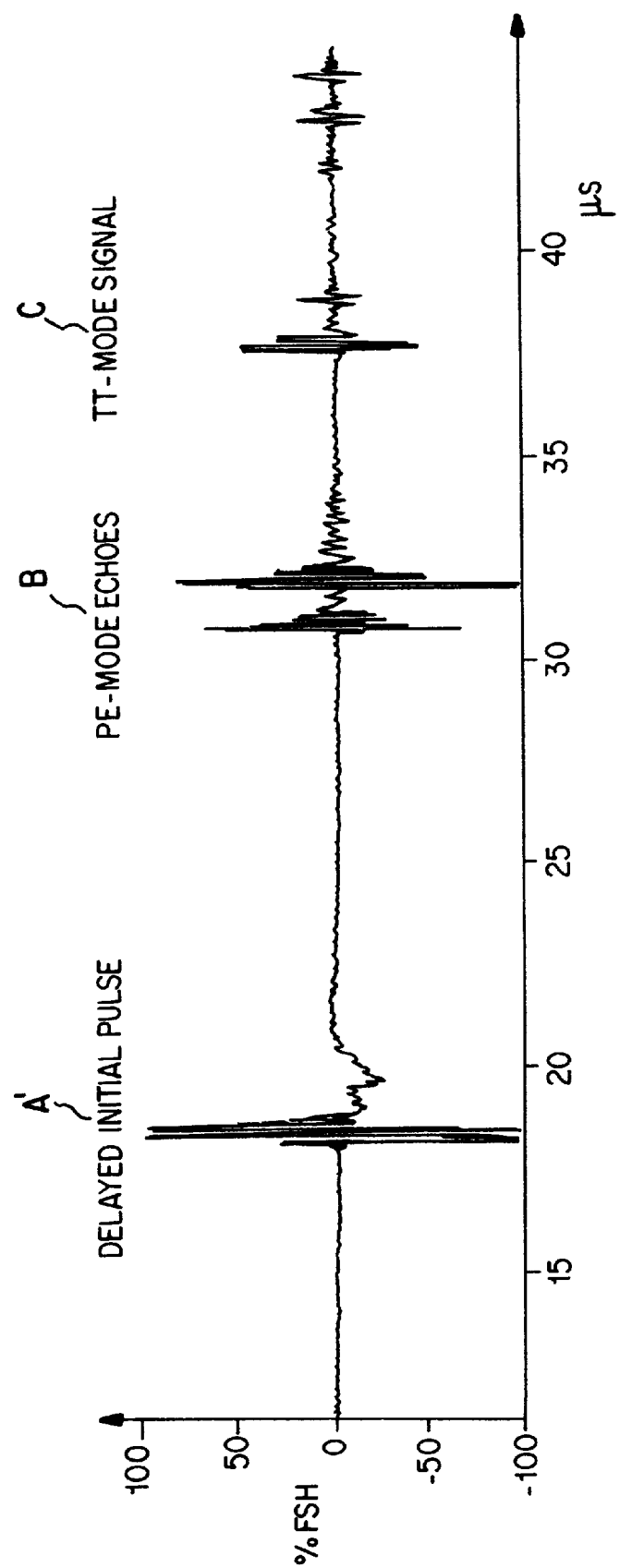
FIG. 10 is an oscillograph of a PE mode signal from transducer 2 combined with the TT mode signal of the system of FIG. 1.
Figure 11:
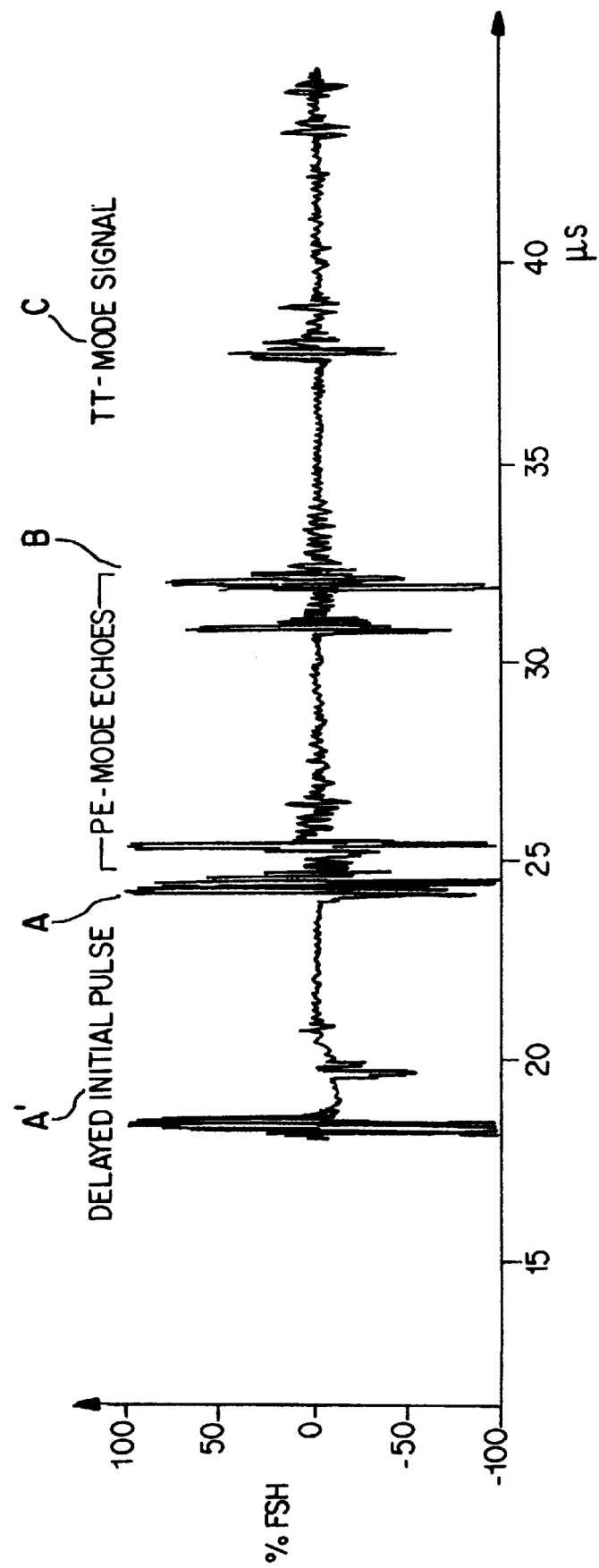
FIG. 11 is an oscillograph of a complete waveform, including PE mode from both transducers, and TT mode received by transducer 1 of the system of FIG. 1.

FIG. 8 is an oscillograph showing PE mode waveform return echoes A from a component under test 9 which are received by transducer 1 of the system shown in FIG. 7. The initial pulse, which energizes the transducer, occurs at a time equal to zero. The time display of this initial pulse begins at approximately 10 microseconds, and is not visible in this example oscillograph. The initial pulse is delayed by the variable delay circuit 10 and generates a delayed initial pulse A' which in turn has corresponding PE mode waveform return echoes B that are received by transducer 2, as shown in FIG. 9. An oscillograph of the PE mode signal from transducer 2 combined with the TT mode signal is shown FIG. 10. The delayed initial pulse A' causes the PE mode echoes B, where the TT mode signal C is received by transducer 1. The complete waveform including PE mode signals from both transducers is shown in FIG. 11. Adjustment of the trigger delay permits the signals of interest to be separated from one another for independent analysis of each mode.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An apparatus for finding locations of interest within an object, comprising:
    an ultrasonic pulser/receiver;
    a first device operatively coupled to the ultrasonic pulser/receiver for transmitting an ultrasonic signal into the object and receiving a return ultrasonic signal reflected from the object;
    a second device operatively coupled to a receiver for receiving the ultrasonic pulse transmitted and passed through the object;
    a mixer coupled to the ultrasonic pulser/receiver and the receiver for combining the transmitted ultrasonic signal and the return ultrasonic signal, and outputting a combined ultrasonic signal; and
    a third device operatively coupled to the mixer for processing the combined ultrasonic signal and outputting the processed combined signal for subsequent display of the locations of interest within the object.

2. The apparatus according to claim 1, further comprising a switching network operatively coupled between the pulser/receiver, the first device, the second device and the receiver.

3. The apparatus according to claim 2, wherein the switching network comprises:
    a first RF switch and a second RF switch coupled to an adapter.

4. The apparatus according to claim 3, wherein the adapter is an "T" adapter.

5. The apparatus according to claim 1, wherein the first device is a pulse-echo (PE) transducer and the second device is a through-transmission (TT) transducer.

6. A method for finding locations of interest within an object, comprising the steps of:
    transmitting an ultrasonic signal into the object and receiving a return ultrasonic signal reflected from the object;
    receiving the ultrasonic signal transmitted and passed through the object;
    combining the transmitted ultrasonic signal and the return ultrasonic signal and outputting a combined ultrasonic signal; and
    processing the combined transmitted ultrasonic signal and outputting the processed combined signal.

7. The method according to claim 6, further comprising the step of operatively coupling a switching network to a pulser/receiver and a receiver.

8. The method according to claim 7, wherein the step of operatively coupling the switching network to the pulser/receiver and the receiver comprises the step of operatively coupling an adapter to a first RF switch or a second RF switch.

9. The method according to claim 6, wherein the step of transmitting an ultrasonic signal into the object and receiving a return ultrasonic signal reflected from the object comprises operatively coupling a PE transducer to an ultrasonic pulser/receiver.

10. The method according to claim 6, wherein the step of receiving the ultrasonic signal transmitted and passed through the object comprises the step of operatively coupling a TT transducer to a receiver.

11. The method according to claim 6, wherein the step of combining the transmitted ultrasonic signal and the return ultrasonic signal and outputting a combined ultrasonic signal comprises operatively coupling a mixer to an ultrasonic pulser/receiver and a receiver.

12. The method according to claim 6, wherein the step of processing the combined transmitted ultrasonic signal and outputting the processed combined comprising operatively coupling a device to a mixer.

13. An apparatus for finding locations of interest within an object, comprising:
    a first ultrasonic pulser/receiver;
    a second ultrasonic pulser/receiver;
    a first transducer operatively coupled to the first ultrasonic pulser/receiver for transmitting a first ultrasonic signal into the object and receiving a first return ultrasonic signal reflected from the object;
    a second transducer operatively coupled to the second ultrasonic pulser/receiver for receiving an ultrasonic signal passed through the object and for transmitting a second ultrasonic signal into the object and receiving a second return ultrasonic signal reflected from the object;
    a mixer operatively coupled to the first and second ultrasonic pulser/receivers for combining the first transmitted ultrasonic signal, the first return ultrasonic signal, and the second return ultrasonic signal, and outputting a combined ultrasonic signal;
    a device operatively coupled to the mixer for processing the combined ultrasonic signal and outputting the processed combined signal for subsequent display of the locations of interest within the object; and
    a delay circuit operatively coupled to the device and the second pulser/receiver for delaying the first ultrasonic signal.

14. A method for finding locations of interest within an object, comprising the steps of:

transmitting a first ultrasonic signal into the object with a first transducer operatively coupled to a first ultrasonic pulser/receiver;

delaying the first ultrasonic signal with a delay circuit operatively coupled to a device and a second pulser/receiver;

receiving a first return ultrasonic signal with the first transducer and an ultrasonic signal passed through the object a second transducer coupled to the second ultrasonic pulser/receiver;

transmitting the delayed first ultrasonic signal into the object and receiving a second return ultrasonic signal with the second transducer;

combining the first ultrasonic signal, the delayed first ultrasonic signal, the first return ultrasonic signal, the second return ultrasonic signal, and the ultrasonic signal passed through the object with a mixer operatively coupled to the first and second ultrasonic pulser/receivers; and processing the combined transmitted ultrasonic signal and outputting the processed combined signal with a device operatively coupled to the mixer.

15. An apparatus for finding locations of interest within an object, comprising:

a first device for generating and receiving signals;

a second device operatively coupled to the first device for transmitting the signal into the object and receiving a return signal reflected from the object;

a third device for receiving the signal transmitted through the object, the third device being operatively coupled to a fourth device for receiving the signal transmitted and passed through the object and received by the third device;

a fifth device coupled to the first device and the fourth device for combining the transmitted signal and the return signal, and outputting a combined signal; and a sixth device operatively coupled to the fifth device for processing the combined signal and outputting the processed combined signal for subsequent display of the locations of interest within the object.

16. The apparatus according to claim 15, further comprising a switching device operatively coupled between the first device, the second device, the third device and the fourth device.

17. The apparatus according to claim 16, wherein the switching device comprises:

a first RF device and a second RF device coupled to an adapter.

18. A method for finding locations of interest within an object, comprising the steps of:

transmitting a signal into the object and receiving a return signal reflected from the object using a second device operatively coupled to a first device that generates and receives the transmitted signal;

receiving the signal transmitted and passed through the object using a third device operatively coupled to a fourth device that receives the signal from the third device;

combining the transmitted signal and the return signal and outputting a combined signal with a fifth device operatively coupled to the first device, the second device, the third device and the fourth device; and processing the combined transmitted signal and outputting the processed combined signal with a sixth device operatively coupled to the fifth device.

19. The method according to claim 18, further comprising the step of operatively coupling a switching device to the first device, the second device, the third device and the fourth device.

20. The method according to claim 19, wherein the step of operatively coupling the switching device to the first device and the fourth device comprises operatively coupling an adapter to a first RF device or a second RF device.

21. An apparatus for finding locations of interest within an object, comprising:

a first device for generating and receiving signals;

a second device operatively coupled to the first device for transmitting a first signal into the object and receiving a first return signal reflected from the object and a signal passed through the object;

a third device for transmitting a second signal into the object and receiving a second return signal reflected from the object, the third device being operatively coupled to a fourth device that receives the second return signal;

a fifth device operatively coupled to the first and fourth devices for combining the first transmitted signal, the second transmitted signal, the return signal, and outputting a combined signal;

a sixth device operatively coupled to the fifth device for processing the combined signal and outputting the processed combined signal for subsequent display of the locations of interest within the object; and a seventh device operatively coupled to the sixth device and the fourth device for delaying the first ultrasonic signal.

22. A method for finding locations of interest within an object, comprising the steps of:

generating a first ultrasonic signal with a first device and transmitting the first ultrasonic signal into the object with a second device operatively coupled to the first device;

delaying the first ultrasonic signal with a third device operatively coupled to a fourth device and a fifth device;

receiving a first return signal and a signal passed through the object with the first device;

transmitting the delayed first signal into the object and receiving a second return signal with a sixth device coupled to the fifth device;

combining the first signal, the delayed first signal, the first return signal, the second return signal, and the signal passed through the object with a seventh device operatively coupled to the second and fifth devices; and processing the combined transmitted signal and outputting the processed combined signal with an eighth device operatively coupled to the seventh device.

23. An apparatus for finding locations of interest within an object, comprising:

an ultrasonic pulser/receiver;

a first transducer operatively coupled to the ultrasonic pulser/receiver for transmitting an ultrasonic signal into the object and receiving a first signal representing a reflected return ultrasonic signal from the object;

a second transducer operatively coupled to a second receiver for receiving a second signal representing the ultrasonic signal transmitted from the first transducer that has passed through the object;

a data acquisition and processing device operatively coupled to the ultrasonic pulser/receiver and the second receiver so as to receive the first and second signals, the data acquisition and processing device being arranged so as to process and combine the first and second signals for subsequent display of the locations of interest within the object.

24. A method for finding locations of interest within an object, comprising the steps of:

transmitting an ultrasonic signal into the object and receiving a return ultrasonic signal reflected from the object;

receiving the ultrasonic signal transmitted and passed through the object; and processing the transmitted ultrasonic signal passed through the object and the return ultrasonic signal and generating a processed combined signal.

* * * * *